United States Patent [19]

Tabacco et al.

[11] Patent Number: 4,567,150

[45] Date of Patent: Jan. 28, 1986

[54] METHOD FOR DETERMINING TRANSFERRIN AND COMPOSITION THEREFOR

[75] Inventors: Alessandro Tabacco, Siena; Paolo Tarli, Monteriggioni; Paolo Neri, Siena, all of Italy

[73] Assignee: Sclavo, S.p.A., Siena, Italy

[21] Appl. No.: 571,859

[22] Filed: Jan. 18, 1984

Related U.S. Application Data

[63] Continuation of Ser. No. 323,360, Nov. 20, 1981, abandoned.

[51] Int. Cl.$^4$ ............................................. G01N 33/90
[52] U.S. Cl. ...................................... 436/87; 436/84; 436/910
[58] Field of Search ....................... 436/910, 84, 87, 74

[56] References Cited

U.S. PATENT DOCUMENTS

| | | | |
|---|---|---|---|
| 3,773,467 | 11/1973 | Yang et al. | 23/230 B |
| 3,887,332 | 6/1975 | Takase et al. | 23/230 B |
| 4,014,651 | 3/1977 | Battinger et al. | 23/230.6 |
| 4,251,360 | 2/1981 | Goldie et al. | 23/230.3 X |

OTHER PUBLICATIONS

Henry, "Clinical Chemistry—Principles and Technics", Harper & Row, 1964, pp. 391–395.
Ramsay, Clinica Chimica Acta, vol. 2, (1957), pp. 221–226.

*Primary Examiner*—Arnold Turk
*Attorney, Agent, or Firm*—Hedman, Gibson, Costigan & Hoare

[57] ABSTRACT

A method for determining the iron-binding capability of transferrin, consisting in adding to the sample being tested a reagent composed of a solution of a ferric salt adsorbed onto a suspension of magnesium carbonate, centrifuging the mixture so obtained and measuring the iron blocked by transferrin in the supernatant. The method is preferably carried out by utilizing a particular composition consisting of a single reagent composed of a suspension of a solution of a ferric salt adsorbed on magnesium carbonate, possibly a medium capable of maintaining the pH between 8 and 9, if desired, a colorimetric reagent for the determination of iron.

7 Claims, No Drawings

METHOD FOR DETERMINING TRANSFERRIN AND COMPOSITION THEREFOR

This is a continuation of application Ser. No. 323,360 filed Nov. 20, 1981 which is now abandoned.

This invention relates to a novel method for the determination of the iron-binding ability of transferrin: it also relates to a particular reactive composition adapted to the purpose.

Transferrin is a glycoprotein contained in the blood and serves to transfer the iron. Each proteinic molecule can bind two ferric ions.

The transferrin blood levels can be measured either directly with immunological methods, or via the determination of its iron-binding ability, with chemical methods.

With respect to the latter methods, it is known, from Chim. Clin. Acta, 2, 221 (1957), a method which provides the steps of:

saturating the transferrin which is present in the sample, usually a serum sample, by an acidic solution which contains an excess of ferric ions.

removing, after an incubation time, the ferric ions in excess, by adding solid magnesium carbonate, and the dosage, upon centrifuging the slurry thus obtained, of the iron bonded to the transferrin which is contained in the supernatant, by means of reagent adapted to the determination of the iron contained in the serum.

Other procedures, conversely, dose, under appropriate conditions, the excess ferric ions and calculate, by difference, the iron removed by transferrin, the amount of transferrin being then determined arithmetically.

The present Applicants have now found that it is quite possible to dose the transferrin which is contained in a sample without previously saturating the sample with an excess of ferric ions in an acidic environment.

A primary objective of the present invention is, in fact, to provide a method which permits the determination of the iron-binding ability of transferrin, said method providing for the use of a single mixture which is composed of a solution of a ferric salt and a slurry of an appropriate solid adsorbent the latter being added to the sample, whereafter the entire mixture is centrifuged and the iron bonded to the transferrin which is contained in the supernatant is determined.

A number of advantages are achieved over the prior art method outlined above and the most significant of them can be summarized as follows:

The procedure is simplified and the number of steps and incubation is lower,

Fewer manipulative steps are required since it is no more necessary to introduce the magnesium carbonate in the solid state into the reaction mixture, The dosage of the reagents is better reproducible, and Transferrin is saturated in the sample with ferric ions and a basic pH, the latter being suggested by the literature as the most suitable for the ability of transferrin to bind iron.

It is a considered opinion of the present Applicants that these facts entail a simplification and an accuracy of determination which cannot be found in the prior art methods.

More detailedly, the method according to the present invention is carried out with the following steps:

Adding to the sample being tested a single mixture consisting of a solution of a ferric salt and an adsorbing solid phase, at a pH comprised between 8 and 9, Centrifuging the final slurry so obtained and Measuring the iron bonded to the transferrin which is contained in the supernatant.

A second important objective of the present invention is to provide, for carrying out the method outlined above, a particular composition, also an integral part of this invention, which consists of a single reagent composed of a solution of a ferric salt adsorbed onto a solid substrate, possibly a medium capable of maintaining the pH between 8 and 9 and, possibly also, a colorimetric reagent for the determination of iron.

Solid substrates adapted to this purpose are members selected from the group consisting of magnesium basic carbonate and $CaCO_3$, magnesium basic carbonate is preferred.

The possible buffer adapted to maintain the pH at a constant value is a member selected from the group consisting of $H_3PO_4$, $H_2PO_4^-$, barbituric acid, barbiturates: $NaH_2PO_4$ is preferred.

If a colorimetric reagent is used, this shall preferably be selected from among those suggested by the conventional art, or, also, it can be the reagent disclosed and claimed in the U.S. patent application Ser. No. 215.176 filed on Dec. 11, 1980, now U.S. Pat. No. 4,407,962 in the name of the Applicants hereof.

Additional details and the operative procedures for carrying out the metering of transferrin will become apparent from the scrutiny of the illustrative nonlimiting examples reported hereinafter.

EXAMPLE 1

Preparation of a Reagent Suspension

In 100 mls of water there are dissolved 828 mg of $NaH_2PO_4.H_2O$ and, thereafter, 2.5 g of basic $MgCO_3$ are slurried: to the suspension so prepared there is added with stirring, 1 ml of 0.01-normal HCl containing 500 mg/dl of $Fe^{+++}$(milligrams per 0.1 liter). The reagent is allowed to stand until pH is stabilized.

EXAMPLE 2

The reagent described in EXAMPLE 1 is used for determining the iron-binding power of a pool of human sera for 48 times and an average value of 293.71 micrograms/dl of iron is obtained, with a C.V. of 3.48%.

The procedure which has been adopted was as follows:

| Reagent Suspension | 1 ml |
|---|---|
| Human blood serum | 0.2 ml |
| Incubation | 5 minutes at room temperature |
| Centrifuging | 10 minutes at 4,000 RPM |

Iron in the supernatant was drawn and dosed with a conventional reagent.

EXAMPLE 3

To fractional samples of a base serum in which the iron-binding power has been determined, progressively increased amounts of human transferrin have been added.

The serum samples so enriched are sampled according to the procedure set forth in EXAMPLE 2 above and according to the Ramsey procedure disclosed in the above cited Chimica Clinica Acta, 2, 221 (1957). The values of the iron-binding power as obtained with said two procedures are correlated with the amount by weight of the added transferrin and the following regression lines are obtained:

x = milligrams (mg) of added transferrin,
y = iron-binding power, in terms of micrograms/dl of found iron, Procedure according to this invention y = 0.90x + 277.2 micrograms/dl with a correlation coefficient = 0.998

Ramsay's Procedure y = 0.91x + 277.5 micrograms/dl with a correlation coefficient = 0.997

The value of the iron-binding power of the base serum evaluated with the method of this invention was 281 micrograms/dl, and, with the Ramsay's method it was 272 micrograms/dl, both these values being in satisfactory agreement with the values of the respective interceptions on the equations of the straight lines reported above.

Concentration ranges of the components of the reagent:
Magnesium basic carbonate: 0.5–10 g/dl
$Fe^{+++}$ from 1 to 100 mg/dl
$H_2PO_4^-$ from 0 to 200 mg/liter.

We claim:

1. A method for determining transferrin comprising the steps of adding to the sample being tested a reagent comprising a solution of a ferric salt adsorbed on an aqueous suspension buffered to a pH of between 8 and 9 of a solid substrate selected from the group consisting of basic magnesium carbonate and calcium carbonate, centrifuging the mixture thus obtained, and measuring the iron bonded by transferrin in the supernatant liquor.

2. Method for determining transferrin according to claim 1, characterized in that the solid substrate is calcium carbonate.

3. Method for determining transferrin according to claim 2, characterized in that the buffer is a member selected from the group consisting of phosphoric acid, phosphates, barbituric acid and barbiturates.

4. A composition adapted to determining transferring consisting of a solution of a ferric salt combined with a solid adsorbent phase selected from the group consisting of magnesium carbonate and calcium carbonate and a buffer means capable of maintaining the pH between 8 and 9.

5. Composition adapted to determining transferrin according to claim 4, characterized in that the buffer means is a member selected from the group consisting of phosphoric acid, phosphates, barbituric acid and barbiturates.

6. A composition adapted to determining transferrin consisting of a solution of ferric salt combined with a solid adsorbent phase selected from the group consisting of magnesium carbonate and calcium carbonate, a buffer means capable of maintaining the pH between 8 and 9, and a colorimetric reagent for the determination of iron.

7. A composition as defined in claim 6 which includes from 0.5–10 g/dl of basic magnesium carbonate and from 1–100 mg/dl of ferric ion.

* * * * *